United States Patent
Bert et al.

(10) Patent No.: US 10,252,082 B2
(45) Date of Patent: Apr. 9, 2019

(54) PLANNING THE IRRADIATION OF A PARTICLE BEAM WHILE TAKING INTO CONSIDERATION A MOVEMENT OF A TARGET VOLUME

(71) Applicant: GSI Helmholtzzentrum Für Schwerionenforschung GmbH, Darmstadt (DE)

(72) Inventors: Christoph Bert, Uttenreuth (DE); Alexander Gemmel, Erlangen (DE); Dirk Müssig, Mömlingen (DE); Robert Lüchtenborg, Münster (DE)

(73) Assignee: GSI Helmholtzzentrum für Schwerionenforschung GmbH, Darmstadt (DE)

( * ) Notice: Subject to any disclaimer, the term of this patent is extended or adjusted under 35 U.S.C. 154(b) by 400 days.

(21) Appl. No.: 14/651,884

(22) PCT Filed: Oct. 18, 2013

(86) PCT No.: PCT/EP2013/071858
§ 371 (c)(1),
(2) Date: Jun. 12, 2015

(87) PCT Pub. No.: WO2014/090456
PCT Pub. Date: Jun. 19, 2014

(65) Prior Publication Data
US 2015/0306424 A1    Oct. 29, 2015

(30) Foreign Application Priority Data
Dec. 14, 2012 (DE) .......................... 10 2012 112 348

(51) Int. Cl.
*A61N 5/10* (2006.01)

(52) U.S. Cl.
CPC ......... *A61N 5/1037* (2013.01); *A61N 5/1031* (2013.01); *A61N 5/1044* (2013.01);
(Continued)

(58) Field of Classification Search
None
See application file for complete search history.

(56) References Cited

U.S. PATENT DOCUMENTS

2008/0023644 A1* 1/2008 Pedroni .................... A61N 5/10
250/400
2008/0081991 A1    4/2008 West
(Continued)

FOREIGN PATENT DOCUMENTS

CN    102089034 A    6/2011
CN    102725029 A    10/2012
(Continued)

OTHER PUBLICATIONS

Japanese Office Action, Application No. 2015-546905, Applicant: Yuzuru Okabe, et al., dated Apr. 15, 2016.
(Continued)

*Primary Examiner* — Andrew Smyth
(74) *Attorney, Agent, or Firm* — Reising Ethington, PC (57) ABSTRACT

A method is disclosed for irradiation planning for the irradiation of a moving target volume located in a body with a particle beam irradiation facility by means of rescanning, which method has the steps of defining the target volume in a reference condition of the motion, dividing the target volume among a plurality of target points that can be individually approached with a particle beam, calculating a nominal dose to be deposited in each of the target points of the target volume, defining a number of rescanning passes in which each of the target points of the target volume are approached, calculating a mean motion to be expected of the
(Continued)

target points of the target volume based on a motion model, taking into account the mean motion to be expected of the target points of the target volume in the irradiation planning in such a manner that the deviation of the expected dose deposition from the nominal dose for each target point is determined, and the nominal dose for each target point is corrected on the basis of the deviation, and generation of control parameters for the irradiation facility, wherein the control parameters comprise a particle count per target point and rescanning pass to be applied.

20 Claims, 5 Drawing Sheets

(52) U.S. Cl.
 CPC .......... *A61N 5/1065* (2013.01); *A61N 5/1049* (2013.01); *A61N 2005/1072* (2013.01)

(56) References Cited

U.S. PATENT DOCUMENTS

| | | | |
|---|---|---|---|
| 2010/0301235 A1* | 12/2010 | Bert | A61N 5/103 250/492.3 |
| 2011/0027853 A1* | 2/2011 | Bert | A61N 5/1048 435/173.1 |
| 2011/0297849 A1* | 12/2011 | Bert | A61N 5/10 250/492.1 |
| 2011/0309255 A1 | 12/2011 | Bert et al. | |
| 2012/0002786 A1 | 1/2012 | Bani-Hashemi et al. | |
| 2012/0238795 A1 | 9/2012 | Bert et al. | |
| 2014/0005464 A1* | 1/2014 | Bharat | A61N 5/1031 600/1 |

FOREIGN PATENT DOCUMENTS

| | | | | |
|---|---|---|---|---|
| DE | 102007045879 | | 4/2009 | |
| DE | 102008027485 | | 12/2009 | |
| DE | 102008036478 | | 2/2010 | |
| DE | 102009055902 | | 6/2011 | |
| DE | 102012112348 | * | 6/2014 | ........... A61N 5/1037 |
| DE | 102012112348 | * | 11/2014 | ........... A61N 5/1037 |
| EP | 2931369 B1 | | 5/2017 | |
| JP | 2008080131 A | | 4/2008 | |
| JP | 2008154627 A | | 7/2008 | |
| JP | 6105081 B2 | | 3/2017 | |
| KR | 101662762 B1 | | 10/2016 | |
| WO | 2010015358 | | 2/2011 | |
| WO | 2012123894 | | 9/2012 | |

OTHER PUBLICATIONS

Chinese Office Action, Application No. 201380072785.7, Applicant: GSI Helmholtzzentrum fur Schwerionenforschung GmbH, Title: Planning the Irradiation of a Particle Beam While Taking into Consideration a Movement of a Target Volume, dated Oct. 8, 2016.

PCT Int. Search Report and Written Opinion, Int. Serial No. PCT/EP2013/071858, Int. Filing Date: Oct. 18, 2013, Applicant: GSI Helmholtzzentrum Fur Schwerionenforschung GmbH, dated Jan. 27, 2-14.

German Office Action, German Serial No. 10 2012 112 348.9, Applicant: GSI Helmholtzzentrum Fur Schwerionenforschung GmbH, dated Dec. 11, 2013.

German Office Action, German Serial No. 10 2012 112 348.9, Applicant: GSI Helmholtzzentrum Fur Schwerionenforschung GmbH, dated Dec. 11, 2013 along with English Translation.

* cited by examiner

PLANNING THE IRRADIATION OF A PARTICLE BEAM WHILE TAKING INTO CONSIDERATION A MOVEMENT OF A TARGET VOLUME

TECHNICAL FIELD

The present disclosure concerns a method and a device for irradiation planning, as well as an accelerator device with a particle beam.

BACKGROUND

Tumor therapy with heavy ions has come to be an established method for treating tissue, in particular tumor diseases, over the course of recent decades. However, the experience gained thereby is also applied in purely technical areas, such as within the scope of research activities or product development activities, where inanimate material is used.

A common feature of all known methods is that a focused particle beam provided by an accelerator is conducted to one or more irradiation or treatment rooms by means of a high energy beam transport system. In the irradiation room, a target volume to be irradiated is positioned, and irradiated with the particle beam.

It is known that a target volume to be irradiated can move. For example, a lung tumor which moves as the patient breathes may be located in the target volume. For example, in order to investigate the effect the motion has on the treatment success of the particle therapy, the motion can be simulated by means of non-living model bodies referred to as phantoms, and such a phantom can be irradiated with the particle beam.

It is a particular challenge in the context of particle therapy to achieve the most homogeneous distribution possible of the radiation dose deposited in the tissue. One reason homogeneous dose distribution in the target volume is of particular interest is the fact that the cells of the tumor located in the target volume only die with adequate reliability at or above a threshold dose, while at the same time, excessive irradiation burden to the surrounding healthy tissue should be avoided. Thus, in irradiation methods in which a plurality of individual radiation doses are to be successively deposited in various target points in the target volume, which is to say with a scanned particle beam, it is still difficult to achieve this desired homogeneous dose distribution in the target volume if the target volume moves during irradiation. Improvement of the homogeneity of dose distribution in target volumes thus remains the subject of current research.

For example, in the case of a scanned particle beam, one possibility is to distribute the radiation dose to be administered over several passes, which is called "rescanning." In this method, the target points of the target volume are approached multiple times so that the total dose to be administered is built up successively by multiple individual doses administered repeatedly during the rescanning passes. Repeatedly approaching the target points with individual doses makes it possible to reduce the effect of the motion on the total dose distribution in the target volume through statistical averaging over the individual doses. In other words, any incorrectly deposited doses can be averaged, statistically speaking, and motions of the target volume can be at least partly compensated for in this way.

Nevertheless, in this context it is necessary to accept the fact that it is not possible to sharply separate the edge region of the target volume, in particular, from the material surrounding the target volume, such as healthy tissue. In order to ensure that the desired nominal dose is administered to the greatest degree possible in the entire target volume, safety margins are typically established around the target volume that significantly increase the actually irradiated clinical target volume. As a result, however, tissue that may be healthy must be irradiated in order to ensure reliable dose coverage in the target volume.

In addition, it is known to track the motion of the target volume within the framework of the gating method used as an alternative to the rescanning method.

GENERAL DESCRIPTION

Therefore, the object of the present disclosure is to provide a method that simplifies irradiation planning for a target volume, and that in doing so diminishes or eliminates the aforementioned disadvantages of the prior art.

Another object of the present disclosure is to make the irradiation result more robust to changes, such as motions, of the target volume.

It is also desirable for the present disclosure to reduce the time required for the full treatment or dose application.

Finally, it is an object of the present disclosure to better omit material adjacent to the target volume, such as healthy tissue or organs at risk, and to irradiate a smaller amount of healthy tissue.

The object of the present disclosure is attained by the subject matter of the independent claims. Advantageous enhancements of the present disclosure are defined in the dependent claims.

Irradiation planning for a target volume located in a body, which process creates, step by step, the irradiation plan for later irradiation with the particle beam, is defined according to the present invention using the following steps:

First a target volume is defined, which typically is located in a body. The target volume in this context can be located in an inanimate body such as, e.g., a material sample, a phantom, or a test setup, or else can comprise living material such as, e.g., cell samples or experimental animals. For example, tumor cells are located in the target volume. The technical terms used in the present document, for example target volume, target point, nominal dose, dose distribution, etc., are used in the customary way for the field and are defined in the ICRU Report 50 (with the Addendum Report 62), which represents an accepted guideline.

The target volume is defined in a reference condition of the motion of the body and/or of the target volume. In other words, this is a moving target volume, where a reference phase is discernible or can be defined in the motion of the target volume. An especially simple example of a motion with reference phase is lung respiration, which is to say a cyclic breathing motion. The end of the exhalation or the start of the inhalation can be defined as the reference phase of breathing, for instance. For example, one respiration cycle corresponds to the sum of the motion phases (planned out in advance) of the motion of the target volume. However, other moving target volumes are also included, for which at least one reference phase of the motion can be defined, and hence the irradiation with the particle beam can be correlated with the motion.

The target volume is subdivided into a plurality of individually approachable target points. In order to be able to approach the target points of the target volume individually with the particle beam, the particle beam preferably is deflected with small changes in direction shortly before emerging from the vacuum, which is to say shortly before striking the target volume. Preferably, deflection magnets, such as those from the raster scanning device of the applicant, can be used for this purpose.

In other words, a raster of target points with defined point spacings is placed in the target volume. Preferably the point spacings are defined in the directions that correspond to the longitudinal primary direction of propagation of the particle beam and/or the directions transverse thereto. The primary direction of propagation of the particle beam in this context is the imaginary axis along which the undeflected particle beam travels. Accordingly, therefore, the point raster can preferably correspond to a Cartesian coordinate system, where the x and y directions correspond to the horizontal or vertical perpendiculars with respect to the primary direction of propagation of the particle beam, and, moreover, the z direction corresponds to the (longitudinal) penetration depth of the particle beam in the material.

In each individual irradiation process, wherein an individual dose is administered to a target point of the target volume by the particle beam of the particle irradiation system, the entire entry path of the particle beam in the body in which the target volume is located receives a dose amount referred as the pre-dose. In the resource-intensive irradiation planning method, all pre-doses that arise must be taken into account and used to calculate the total dose. Thus, it may be desirable, for example, to first irradiate the distal end of a target volume, in which process the more proximal part of the target volume is already subjected to a pre-dose. The target volume can then be irradiated from the opposite direction, for example, so that the part of the target volume that is distal from this end receives an additional sub-dose. Alternatively, the target volume can continue to be irradiated from the same direction in further rescanning passes, and the more proximal part irradiated with a weaker dose, which is to say, for example, with a lower particle count, so that the nominal dose for each target point is ultimately reached and the total dose in the target volume is distributed as homogeneously as possible. In the ideal case, the total dose distribution over the target volume corresponds to a step function. This is, by its nature, achievable only with difficulty in practice.

A nominal dose, which is to say the planned or desired value of the radiation dose to be deposited in the applicable target point, is associated with each of the target points. In other words, the irradiation planning calculates the nominal dose to be deposited in the applicable target points and writes the result in the irradiation plan.

The nominal dose is also divided among a number of rescanning passes, with at least a portion of the target points being approached in each pass. Preferably, all the target points are approached in each rescanning pass of the particle beam, and if applicable the rescanning passes are also identical to one another with respect to the approach to the target points. Especially in the circumstance when the same target points are approached in each rescanning pass, or when the rescanning passes are identical, the statistical averaging effect of the rescanning method arises.

In other words, therefore, a number of rescanning passes in which the target points of the target volume are each approached is already defined in the irradiation planning. An effect of the division of the nominal dose among rescanning passes is that if, for example, an unanticipated motion of the target volume later takes place during the application of the dose to one of the target points, as a result of which the dose to be administered is not deposited in the target point but rather is deposited incorrectly, then this can be compensated for statistically, at least in part, by the preceding or subsequent rescanning passes.

In a simple case, the target points of the moving target volume move in the same direction in the body so that the target volume carries out a translation essentially undeformed and the point lattice of the target points remains uniform. However, the motion of the target points of the target volume can also take place relative to one another. For example, the target volume can be expanded, squeezed, stretched, or otherwise deformed, and density variations in the target volume or in the surrounding material can also be significant for the penetration depth of the particle beam, so that the target points are displaced correspondingly. A superposition of a translation with a deformation of the target volume should also be taken into account, and is likewise understood as a motion of the target volume.

A motion model is available that permits conclusions to be drawn concerning the motion to be expected of the target volume and/or the motion of the target points of the target volume. A patient model, a mathematical (motion) function, a 4D CT scan and/or a breathing study can be taken into account as the basis for determining the motion model. The breathing study can be carried out for a single target volume or for a large number of target volumes, for example in the form of a patient survey, so that an average expected motion of the target points of the target volume, for example a lung tumor, can be predicted. For example, the weighted average of the dose contributions from the anticipated motion conditions is taken into account for determining the motion model.

The motion model, which predicts the motion of the target points of the target volume, can be used for irradiation planning to determine the deviation of the motion-free nominal dose from the dose deposition that is to be expected when taking the motion into account. This means that an analysis of the motion model in advance of the irradiation, which is to say as part of irradiation planning, can increase the homogeneity of dose deposition and/or the conformity, which is to say the edge sharpness of the dose deposition, in the event of a rescanning method with a scanned particle beam. The motion model is also used with regard to detection of motion phases and irradiation with the particle beam is temporally correlated with at least one motion phase, for example the reference phase. In this way, a saving of time as compared to alternative methods, can be preserved in that the time period of the irradiation includes at least multiple motion phases or even includes the entire motion process of the target volume. Moreover, the homogeneity of the dose distribution that can be achieved by rescanning, and the sharpness of the dose deposition in the target volume edge region, the conformity, can be significantly improved so that safety margins around the target volume, which may have to be placed in healthy tissue or even in organs at risk (OAR), can be reduced or even eliminated entirely.

The mean motion to be expected of the target points of the target volume can be taken into consideration by a correlation of the irradiation with the movement of the target points of the target volume by the means that the nominal dose at each target point is corrected on the basis of the deviation found. In detail, the nominal dose can be adjusted, for example, by a change in the particle count to be deposited in the target point, wherein the total particle count is distributed among the rescanning passes and wherein the individual particle counts for each rescanning pass can also be different. For example, it may be desirable in the case of a known motion of the target volume, especially when density variations exist in the target volume, to deposit a high particle count in the target point in one phase of the motion, but to deposit only a low particle count in another phase of the motion in order to thus obtain the optimum homogeneity of the dose distribution in the target volume through the effect of statistical averaging. In other words, the approach to selected target points of the target volume can be correlated with the motion condition of the target volume. As a result of taking the motion into consideration in the irradiation planning, the edge region of the dose deposition in the target volume can be defined more sharply on the whole, and the irradiation burden on the material surrounding the target volume, such as, for example, healthy tissue or organs at risk, can be reduced.

Finally, control parameters are generated for the irradiation facility from the data obtained regarding the target points, the motion, and the resultant deviation of the target points of the target volume due to the motion, so that the desired, corrected nominal dose can be deposited for each target point using the irradiation facility. For example, the control parameters comprise the particle count per target point and rescanning pass to be deposited in the target volume.

The target points can be assigned to iso-energy layers of the particle beam. This makes it possible to irradiate the target points of an iso-energy layer with constant particle energy, which is to say, for example, unchanged accelerator settings. In other words, it may be desirable to approach the portions of the target points that are combined into iso-energy layers consecutively in order to change the accelerator settings less often, and thus to shorten the time that the overall irradiation process takes.

The expected dose distributions for the target points of the target volume can for example be calculated for the iso-energy layers of the particle beam. Preferably, the iso-energy layers are each approached upon the occurrence of a defined motion condition, which is to say, for instance, the reference condition of the motion. In other words, the start (the approach) of an iso-energy layer can be synchronized with a specific motion phase. This can further improve the robustness of the dose distribution to motions of the target volume.

Furthermore, it resides within the scope of the present disclosure to propose a method for irradiating a moving target volume located in a body with a particle irradiation facility by means of rescanning. The irradiation method utilizes, for example, the irradiation planning data generated in advance of the irradiation by the means that the irradiation plan is loaded into a control unit of the irradiation facility.

A motion sensing device is used to detect the motion of the target volume during the course of the irradiation, so that the precalculated motion can also be verified and/or corrected during the course of the irradiation on the basis of the actual motion. Based on the data from the motion sensing device, accordingly, additional control parameters for the irradiation facility can be generated, by means of which it is possible to correct the nominal dose planned in advance on the basis of the irradiation planning.

Finally, the control parameters generated on the basis of the irradiation parameters, and the additional control parameters generated on the basis of the motion sensing device, are used to control the particle beam so that the target volume can be irradiated with the particle beam with the motion of the target volume being taken into account.

Within the scope of the present disclosure, an irradiation facility is also provided that is suitable for executing the steps of the above-mentioned method.

The present disclosure is explained in detail below using exemplary embodiments and with reference to the figures, wherein identical and similar elements are in part labeled with identical reference numbers, and the features of the various exemplary embodiments can be combined with one another.

BRIEF DESCRIPTION OF THE FIGURES

Shown are.

DETAILED DESCRIPTION

Figure 1:
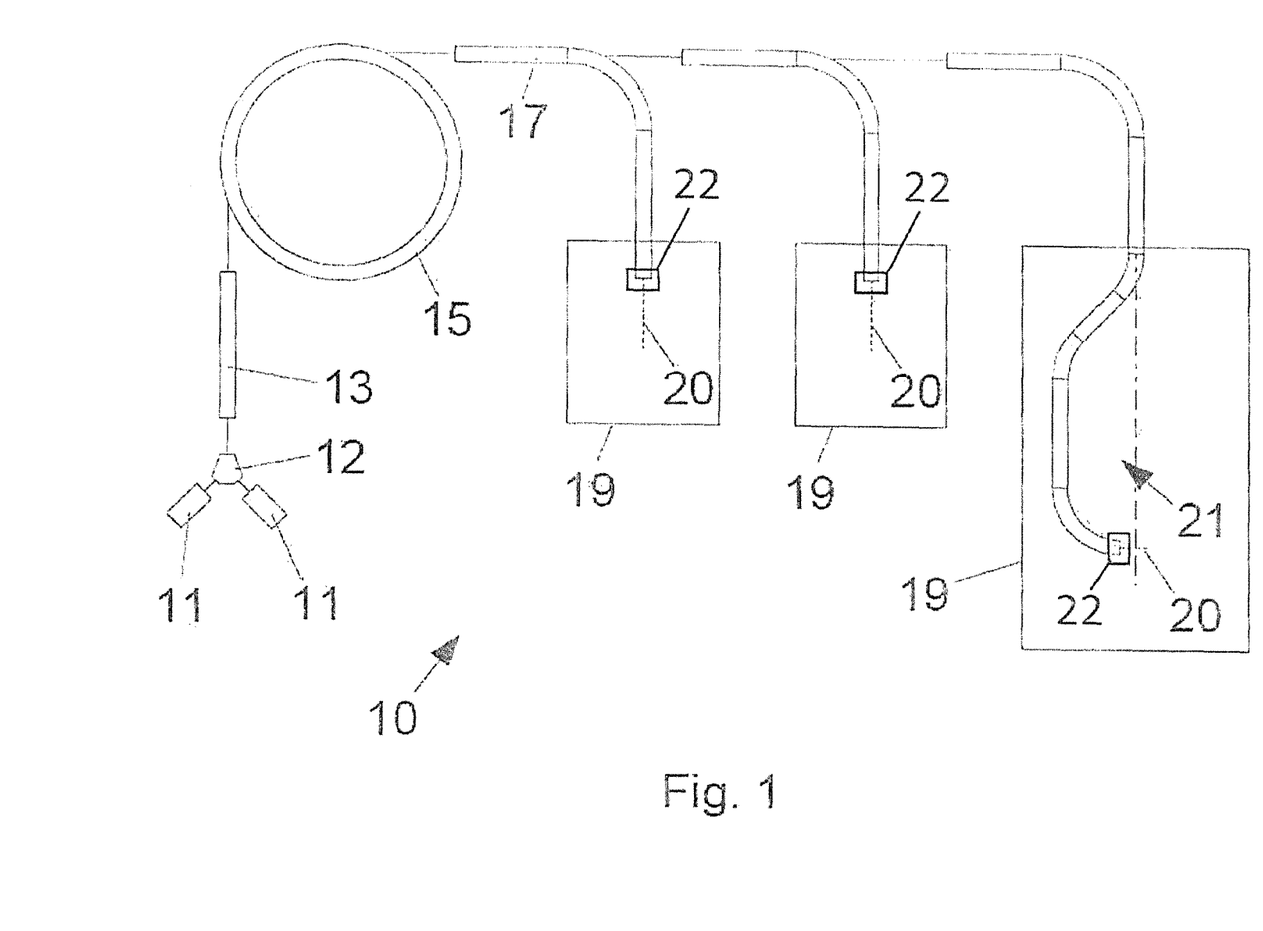
FIG. 1 an overview of the configuration of an irradiation facility that provides a particle beam within the framework of rescanning methods, FIG. 2 a schematic representation of components used to control an irradiation facility, FIG. 3 a schematic representation of a deflection and modulation device and an irradiation of a target volume, FIG. 4 dose distribution change in the target volume obtained using the method according to the present disclosure, FIG. 5 an overview of steps of the method according to the present disclosure.

FIG. 1 shows the schematic configuration of a particle therapy facility 10 that is known per se. The particle therapy facility 10 generates and accelerates charged particles that are provided for further use in the form of a particle beam 20 and can be directed by means of a beam guide 17 into a defined target volume 34 (see FIG. 3). The target volume 34 contains a tumor within the framework of tumor therapy, for example, but a target volume 34 that contains inanimate material and/or cell cultures may also be defined for scientific purposes, animal experiments, model and material samples, and in general for investigating the particle beam and/or particle therapy. The particle therapy facility 10 is also used for irradiating phantoms with the particle beam 20, by which means a plurality of irradiation parameters can be verified before and/or after a completed irradiation or treatment of a patient.

In the example shown in FIG. 1, the particles are generated and pre-accelerated in one of the two ion sources 11. The ion sources 11 can provide, for example, a wide variety of particles from protons to uranium. Protons, pions, helium ions, or carbon ions are used because of their properties for particle therapy, such as the characteristic (particle-dependent) interaction with material and the penetration depth. Speaking very generally, hadrons are preferred for use as particles. By means of a low energy beam transfer line 12, the particles are threaded into a pre-accelerator 13, which in the case shown is the UNILAC (Universal Linear Accelerator) linear accelerator 13. The linear accelerator 13 accelerates the particles to a first energy level, and focuses the particles into a particle beam 20. At the first energy level, the particles are ultimately threaded into the accelerator unit 15, for example, a synchrotron as shown here, but also a cyclotron, with another low energy beam transfer line 12, where they are further accelerated up to the extraction energy, which can be set for the application in question. Finally, the beam guide 17 guides the particle beam 20 to the desired target in a measurement room 19 or therapy room 21, where the particle beam 20, with a typical beam diameter of 3 to 30 millimeters, can be applied or is made available.

For precise positioning of the particle beam 20 in order to approach a target point 30 of a target volume 34 in a body 77, a deflection and modulation device 22 for transverse, which is to say horizontal and vertical, deflection of the particle beam 20 and for energy modulation to rapidly vary the particle beam energy, which determines the penetration depth of the particle beam 20 (longitudinal variation), is located in the measurement or irradiation room 19 or therapy room 21. Since an entire raster of target points in a target volume can be approached successively by this means, and the successive approach of the target points is called "scanning," the device is referred to as raster scanning device 22. However, the present disclosure is not limited to the use of a raster scanning device 22, but instead the irradiation methods of spot scanning, continuous irradiation, and raster scanning can be used.

The order in which the target points 30 of the target volume 34 are approached is set forth in a irradiation plan, which also can contain additional parameters, in particular such as the parameters of the target volume 34 and/or a motion to be anticipated of the target volume 34. One of the effects of the raster scanning device 22 is that it provides the opportunity to direct the particle beam 20 continuously at the target volume 34 without individually activating the beam for approaching the applicable target point 30.

The entire particle therapy facility 10 is ultimately controlled by an accelerator control system that, for example, controls the accelerator unit 15 and the beam guide 17, and collects measurement data for monitoring beam parameters. If appropriate, the parameters for controlling the particle therapy facility 10 can be set based on the irradiation plan, so that the irradiation plan also includes the setting data for controlling the particle therapy facility 10.

Figure 2:
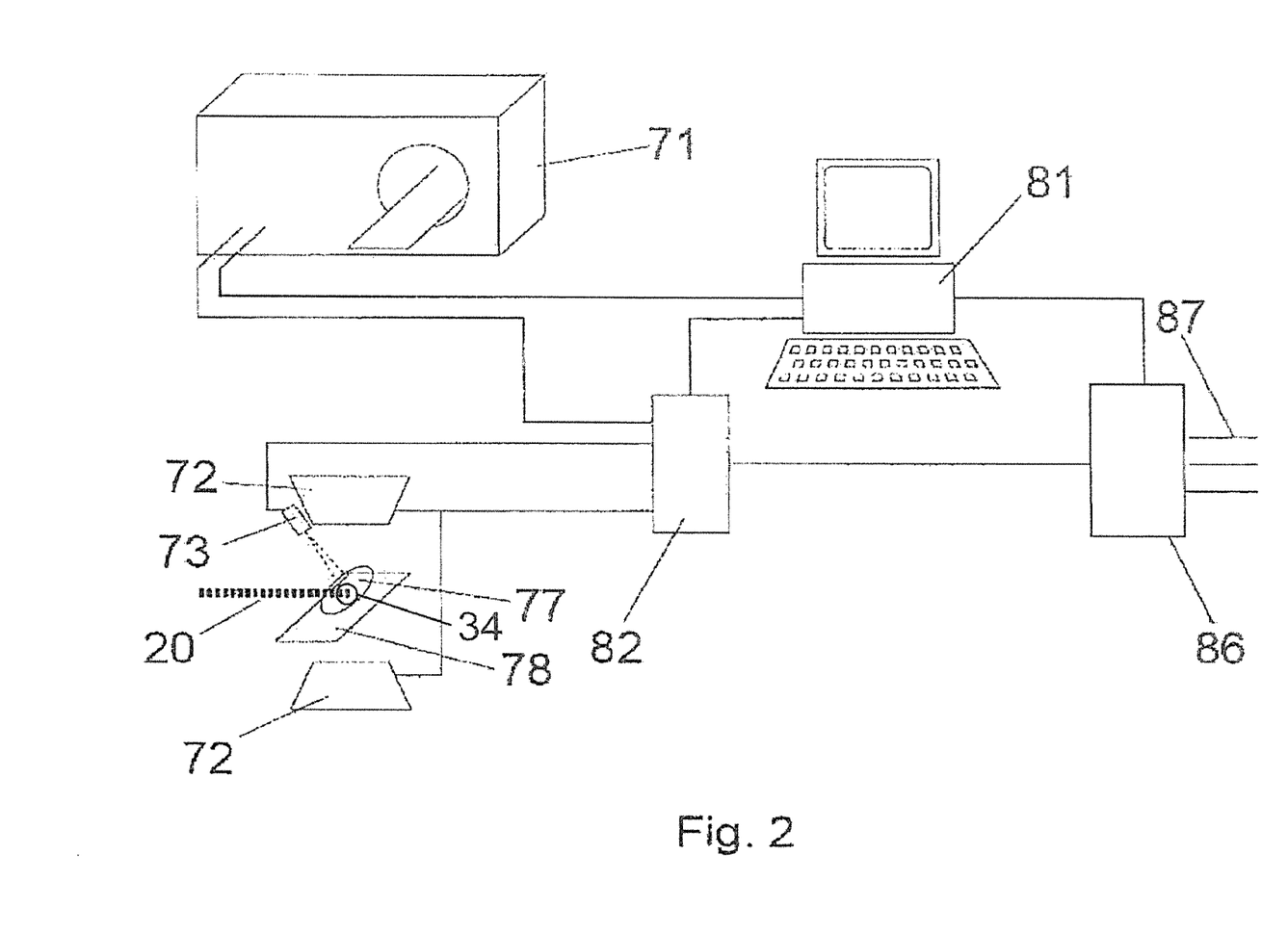

FIG. 2 shows a schematic representation of devices and equipment that are known per se and which can be used in creating an irradiation plan, which is to say in irradiation planning, for creating a data set that defines target points 30 in a target volume 34 in a body 77, and in the control of a particle therapy facility 10 such as was described with reference to FIG. 1, for example.

The position and extent of a tumor to be irradiated or of another target volume 34 can be ascertained by means of a CAT or MRI system 71, or by means of other diagnostic equipment. Data from the tomography system 71 are processed by a device 81 for creating a data set, either directly or after preparation. The device 81 is a workstation, a terminal, or other computer, for example. Due to its user interface, software, or other features, the device 81 is optionally also suitable for medical staff to use for defining the target volume 34, the doses to be administered, the division of the same into multiple fractions, the direction of the irradiation, and other details of the particle therapy.

The body 77 to be irradiated can be monitored using variously implemented monitoring equipment before, during, or after the irradiation by the particle therapy facility 10. Provided by way of example are a PET camera 72 (PET=positron emission tomography) and/or a distance sensor 73 for sensing a body 77 to be irradiated that is supported on a support surface 78. The PET camera 72 and/or the distance sensor 73 and the support surface 78 can be located within one of the irradiation rooms 19 described above with reference to FIG. 1. In this case, the dose produced through a particle beam 20 and motions of the irradiated body 77 can be sensed by means of the PET camera 72 and/or the distance sensor 73. Alternatively, the PET camera 72, the distance sensor 73, and the support surface 78 are located outside of an irradiation room. Alternatively or in addition, the body 77 can be monitored by means of a fluoroscopy device, an X-ray device, an ultrasound sensor, a respiration monitoring belt, and/or other external sensors.

Data from the tomography system 71, from the PET camera 72, and from the distance sensor 73 can be processed by a device 82 for determining one or more motion parameters. By means of the device 82, motions of sub-areas of the body 77 (for example, because of breathing or heartbeats) can be quantitatively sensed before an irradiation or during an irradiation. The motion parameter or parameters determined by the device 82 can be taken into account by the device 81 for creating a data set.

Especially suitable for being taken into account during the creation of a data set are data regarding the amplitudes of typical and/or periodic motions or regarding a relationship between the spatial position of the target volume and/or a quantity that can be sensed from outside, for example, by means of the distance sensor 73. Alternatively or in addition, parameters determined by the device 82 or data can be processed directly by a controller 86 for controlling an irradiation facility 10 such as was described with reference to FIG. 1. Data sensed by the PET camera 72 or the distance sensor 73 during the irradiation are especially suitable for this purpose. The data set created by the device 81 is also incorporated into the control of the facility 10 by the control unit 86. The control unit 86 is linked to the irradiation facility 10 by control lines 87 or by other means.

The basic configuration of an irradiation facility 10 as described with reference to FIG. 1 is typical of many particle therapy facilities and other irradiation facilities. The exemplary embodiments described below can be used in connection with the irradiation facility described with reference to FIG. 1, as well as with the equipment described with reference to FIG. 2, as well as with other irradiation facilities and equipment.

Figure 3:
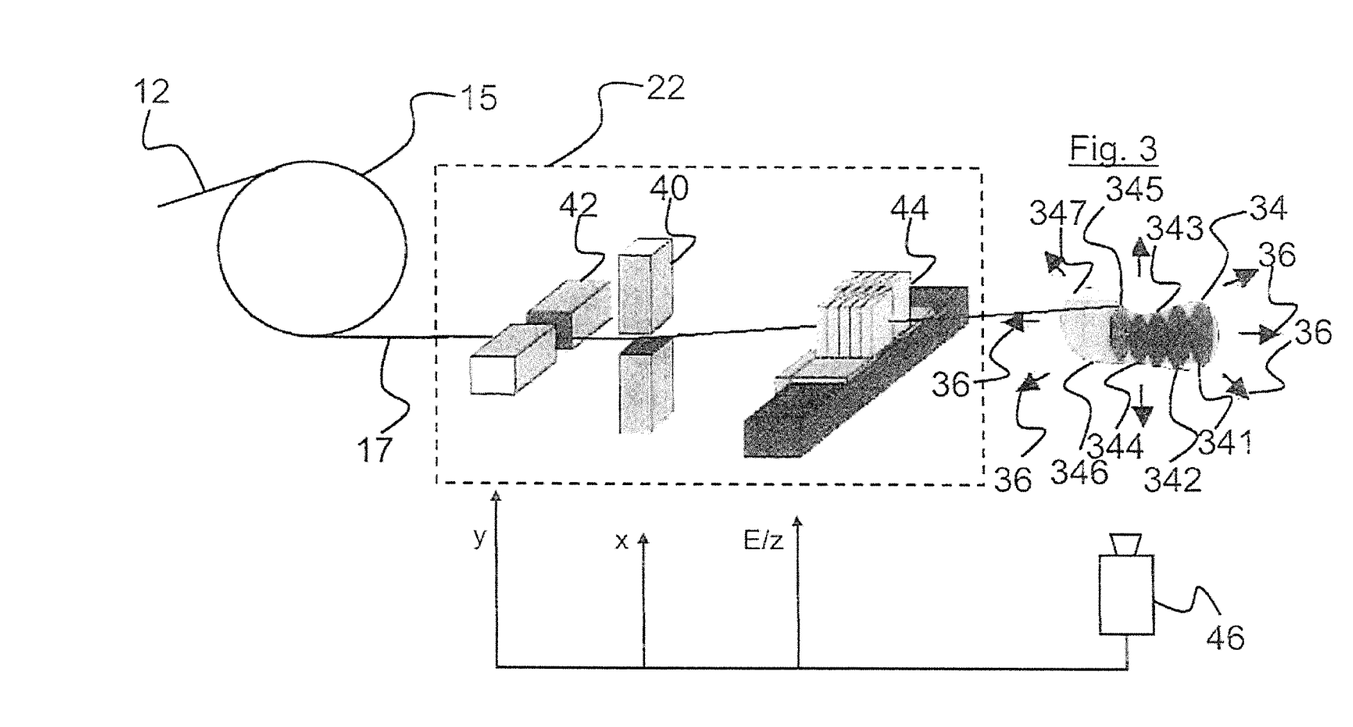

FIG. 3 schematically shows an irradiation of a target volume. The accelerator unit 15 provides the particle beam 20, which is raster-scanned with two scanning magnet pairs 40, 42 transverse to the beam direction of the particle beam, which is to say laterally, over the target volume 34. The target points 30 of the target volume 34 define the point raster of the target volume, wherein the target points are located in a plurality of iso-energy layers, the iso-energy layers 341 to 347 in the example shown. The iso-energy layers 341 to 347 are scanned successively with the particle beam 20. In the embodiment in FIG. 3, the iso-energy layer 345 is in the process of being scanned laterally. A motion of the target volume 34 is indicated by the arrows 36. This motion can be detected by means of a motion sensing device 46, which senses the motion of the body 77.

On its approach to a target point 30, the particle beam 20 deposits a dose distribution, wherein the dose distribution is typically dependent on the profile and diameter of the particle beam employed. Thus, the particle beam can have a round cross-section, so that the dose distribution also decreases concentrically outward from the center point of the beam.

For the person skilled in the art, it is not necessary to explain in detail a three-dimensional dose deposition that may also affect target points 30 of adjacent iso-energy layers 344, 346, the calculation of three-dimensional pre-doses, and the selection of the irradiation sequence of the iso-energy layers, since this individual can already infer the complete irradiation process herefrom and from the figures, and can, for example, likewise adapt the irradiation plan for all iso-energy layers 341 to 347. Thus, the method can easily be translated, using the description and the figures, to target points 30 spatially distributed in the target volume 34.

Figure 4:
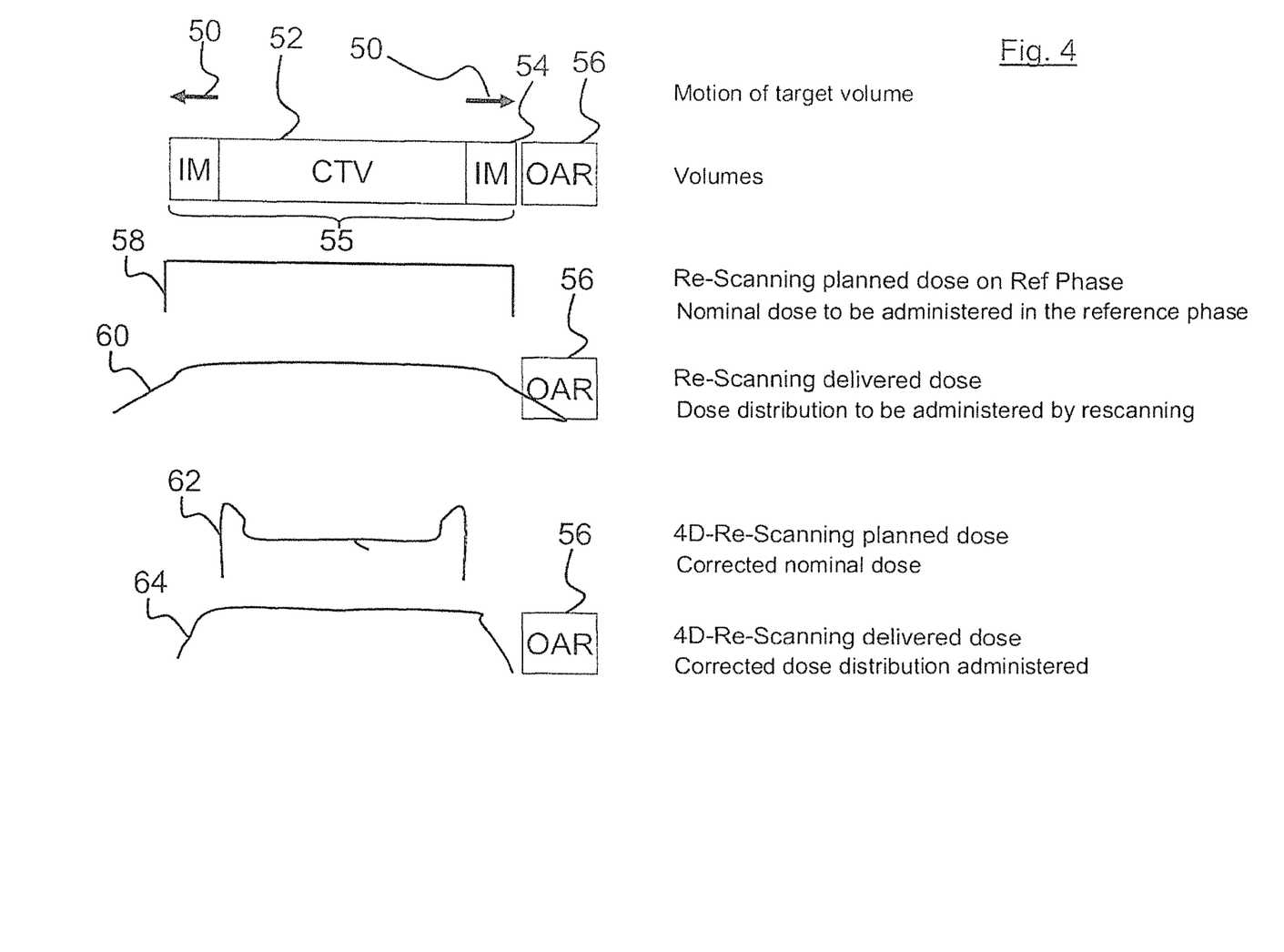

FIG. 4 shows the effect of taking the motion into account on dose distribution in the region of the target volume. The arrows 50 represent the motion, which in the case shown represents a periodic breathing motion. The inner region shows the clinical target volume 52 (CTV, Clinical Target Volume), which is surrounded by safety margins 54 (IM, Internal Margins). The clinical target volume 52 and safety margins 54 together constitute the target volume 55. The target volume 34 described in conjunction with the embodiments in FIGS. 2 and 3 can correspond to the target volume 55. An area at risk 56 (OAR, Organs At Risk), which must be treated with special care, which, in other words, should be exposed to as small a radiation dose as possible, is located next to the target volume 55. The step function 58 shows the nominal dose distribution within the target volume 55 that is usually desired. Consequently, a homogeneous dose that is as low as possible but still lethal should be deposited in the entire target volume 55, which comprises the clinical target volume 52 and the safety margins 54. The distribution curve 60 shows the dose distribution typically deposited in the tissue on the basis of such an uncorrected nominal dose distribution. A significant dose rate is typically also deposited in the area at risk 56.

The corrected distribution curve 62 shows, finally, the corrected nominal dose distribution 62 following correction by the mean motion to be expected of the target points 30 of the target volume 34, 55 as proposed by the present disclosure. Taking the motion into account can thus better adapt the dose distribution in the tissue to the objective of the irradiation, namely, the sufficiently high dose deposition in the clinical target volume 52. The safety margins 54 introduced previously for moving target volumes can thus become narrower, or be eliminated entirely where appropriate, when the method according to the present disclosure is used. Furthermore, better protection of the area at risk 56 takes place.

The distribution curve 64 shows the dose rate deposited in the tissue on the basis of the corrected nominal dose distribution 62. It is a crucial goal of the optimization to adapt the nominal dose distribution to the moving target volume 55, and consequently to limit the region in which a dose rate is deposited as closely as possible to the clinical target volume 52. This is very clearly evident from FIG. 4. The nominal dose distribution 62 corrected in accordance with the present disclosure generates a distribution curve 64 of the dose deposition that has edges that are noticeably steeper and are not as far away from the clinical target volume 52, and thus affect less surrounding material such as healthy tissue or areas at risk 56.

In the example from FIG. 4, it is clearly evident that a lower dose or even no radiation dose at all is deposited in the area at risk 56. The deposited dose rate is lower in the previously defined safety margin 54 as well, with the result that the safety margins can be made narrower or, in the ideal case, can be omitted. Using the method according to the present disclosure, a more homogeneous and/or more conformal corrected dose distribution 64 can be obtained, even under the effects of the motion 36, 50 of the target volume, so that irradiation of the target volume 34, 55 can, where appropriate, also be carried out outside of the reference phase of the motion, thus achieving a significant saving of time.

An example of a mathematical function is discussed below that can be the basis for determining the motion model. In order to get the full dose as close as possible to the "prescribed" nominal dose, which is the goal of optimization by means of the motion model, in the following we shall consider the determination of the particle count for each raster point (without taking into consideration an area of risk 56 to be protected). For example, for a 3D optimization the minimum of the following function F(i, N$_j$) must be sought:

$$F(i, N_j) = \sum_i \left( D_{plan} - D_{i,ref}\left(\sum_j N_j\right) \right)^2$$

where $D_{plan}$ represents the nominal dose and $$D_{i,ref}\left(\sum_j N_j\right)$$

represents the dose deposited in a target point i, 30 in the reference phase of the motion as a function of the particle counts N$_j$ deposited in all target points j, 30. However, only a dose distribution corresponding to the distribution curve 60 can be obtained on the basis of this function. In other words, this function corresponds to the optimization of a static tumor that is used for classic rescanning and requires that safety margins around the tumor be taken into account. This leads to increased irradiation of healthy tissue.

In the novel method proposed for determining the motion, the dose deposited in a target point i, 30 is calculated from the weighted average of the dose contributions from all expected motion conditions m. The function to be minimized could appear as follows, for example:

$$F(i, N_j, P_m) = \sum_i \left( D_{plan} - \sum_m P_m \cdot D_{i,m}\left(\sum_j N_j\right) \right)^2$$

where $$D_{i,m}\left(\sum_j N_j\right)$$

represents the dose deposited in the target point i, 30 in the motion condition m, and P$_m$ represents the probability of striking the target volume 34, 55 in the motion condition m. In other words, the motion of the target volume is explicitly taken into account by means of the motion model. On the basis of this function, it is possible to predict the anticipated dose deposition of each raster point, which deposition can be calculated for each phase of the motion and can be weighted through the probability function. This accordingly permits the optimization on the basis of an actual 4D dose deposition to be expected instead of the previous stationary 3D dose deposition. Accordingly, this is a true 4D optimization, which can increase the conformity of the dose in particular.

In general, this probability function can depend not only on the motion condition m, but also on the position of the target point j, 30. This would be the case, for example, if changes in the motion trajectory were known even before the irradiation, or are artificially induced. For example, the motion state can be defined with the start of the approach of each iso-energy layer, or the particle intensity can be varied during the irradiation. In this case, the function could appear as follows:

$$F(i, N_j, P_{m,j}) = \sum_i \left( D_{plan} - \sum_m \sum_j P_{m,j} \cdot D_{i,m}(N_j) \right)^2$$

The application of the planned nominal dose is thus ensured through the optimization, which, unlike in conventional rescanning, explicitly takes into consideration information from all motion conditions, instead of being ensured solely through defining the safety margins 54. Hence the region in which the dose is deposited can be reduced. This will have the effect, for example, that organs at risk 56 to be protected, which are located in the vicinity of the clinical target volume 52, can be protected better. The decision as to whether the safety margins 54 are reduced or whether they can even be dispensed with where appropriate can either be made manually or can be appropriately adapted in an automatic optimization. A use of conventional safety margins 54 is also possible with the method according to the present disclosure, for instance, in order to achieve improved dose deposition in the case of breathing patterns that deviate strongly from a uniform distribution of the motion conditions, or to be able to better assess the dose deposited in organs at risk 56 including motion effects.

A mean motion of the target points of the target volume can be calculated from the probability functions of the possible development over time of the motion states. Finally, the mean calculated motion of the target points of the target volume can be taken into account in the irradiation planning in order to increase the conformity of the dose deposition.

In addition, the method can be combined with the gating method where appropriate, so that the irradiation only takes place in a selected subset of all motion states. As a result, a larger gating window could be tolerated, for example in comparison with straight gating with target volume 55, and hence the total irradiation period could be reduced. The selection of the gating window can be accomplished manually or can be part of the optimization.

This method can be used in that the path of motions is additionally measured during the irradiation. If too great a deviation in the distribution of the motion phases from the assumed distribution is ascertained, various countermeasures can be taken—for example: pausing (gating) of the irradiation during the dominant motion conditions, replanning for the current or future fraction or fields, modulation of the incident particle intensity (increase during subdominant motion conditions or reduction during dominant motion conditions), and controlled patient breathing, for example by means of breath coaching or artificial respiration.

Figure 5:
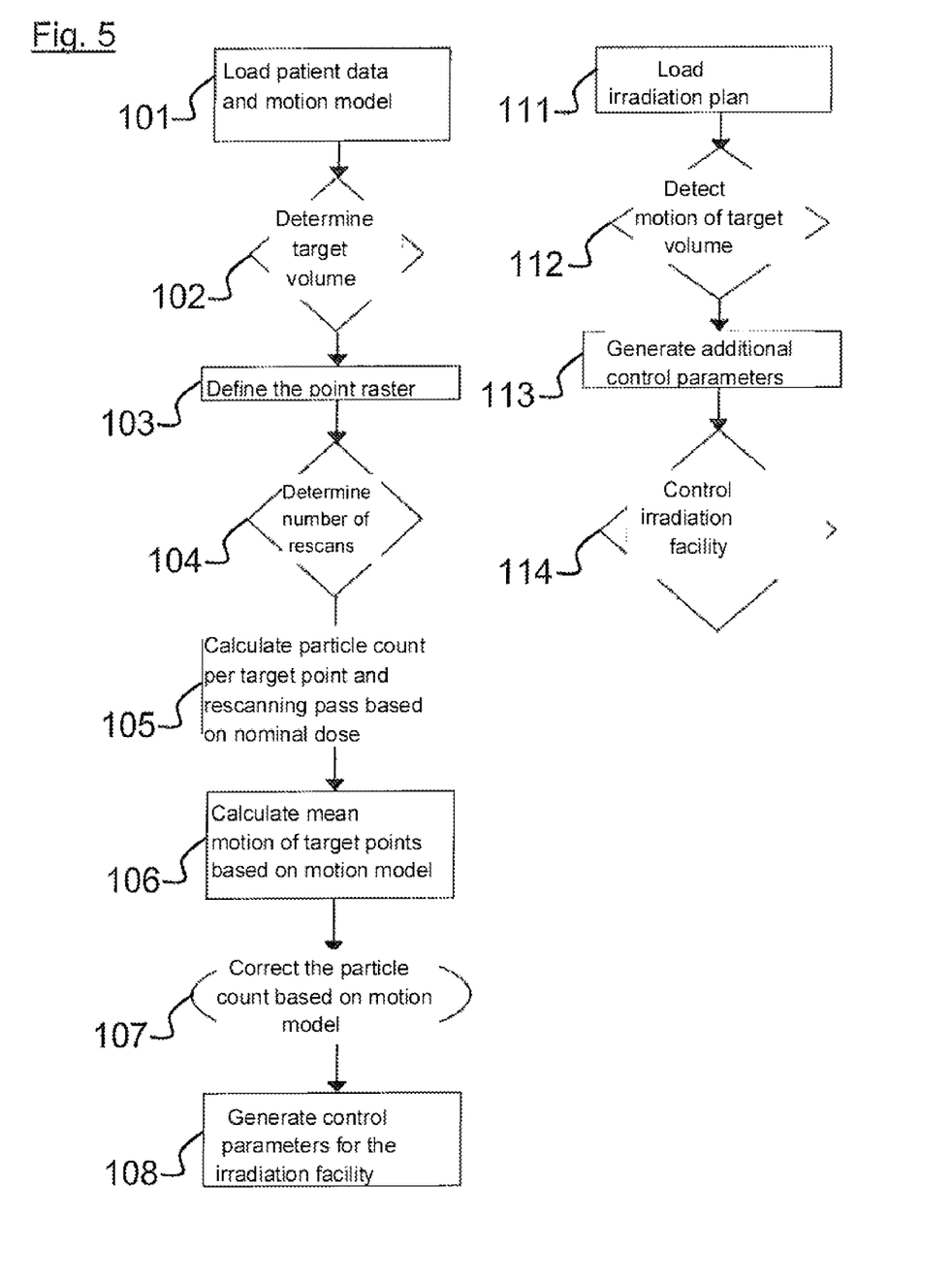

FIG. 5 shows, on the left-hand side, eight steps of the irradiation planning method preceding the irradiation. First, in step 101, the patient data and the motion model to be employed are loaded. For example, the patient data contain information on the dose rate to be applied, the extent of the target volume 34, 55, information on areas at risk 56, and information on density curves in the body 77, so that the particle energies and the individual dose distributions can be calculated. Based on the patient data, the target volume 34, 55 is defined in step 102, and a raster of points, which is to say the target points 30 of the target volume, is defined in step 103.

In step 104, the number of rescanning passes is defined appropriately for the example in FIG. 5. The nominal dose 58 is divided among the rescanning passes for each target point 30.

In step 105, the particle count per target point 30 that is to be deposited with the particle beam 20 of the accelerator system 10 is calculated. The particle count per target point 30 can be calculated on the basis of the nominal dose 58 to be deposited.

In step 106, the selected motion model is applied to the nominal dose distribution 58 in the target volume 34, 55, and the mean motion of the target points 30 is calculated on the basis of the motion model. A correction of the particle count takes place in step 107, with a corrected nominal dose 62 being calculated on the basis of the motion model.

Finally, in step 108, the corrected control parameters corrected on the basis of the motion model—are generated for the irradiation facility, and are thus retrievable in the irradiation plan for a later irradiation session.

The method for irradiating a target volume 34, 55 can comprise the following steps, likewise outlined in FIG. 5. First, in step 111, the irradiation plan is loaded in a control unit 86 for controlling the irradiation facility 10; this plan already contains, in prepared form, the patient data, the data on the target volume and point raster, as well as the corrected nominal dose distribution 62.

By means of a motion sensing device 82, which can quantitatively measure the motions of the target volume 34, 55, in step 112 the motion of the target volume is detected, preferably during the entire irradiation process. Incidentally, where appropriate a monitoring of the correct irradiation process can also be carried out using the motion sensing device 82.

On the basis of the actual motion data of the target volume 34, 55 generated with the motion sensing device 82, additional control parameters are generated in step 113; the control of the irradiation facility 10 can be continuously corrected by means of these control parameters if the actual motion data deviate from the motion data calculated in advance. Any correction to the control of the irradiation facility that may need to be undertaken is carried out in step 114, by means of which the irradiation facility is ultimately controlled with the control parameters and the additional control parameters being taken into account.

It is evident to an individual skilled in the art that the embodiments described above should be considered as examples, and that the invention is not limited thereto, but instead can be varied in multiple ways without departing from the invention. Furthermore, it is evident that, regardless of whether the features are disclosed in the description, claims, figures, or elsewhere, they also define parts of the present disclosure singly, even if they have been described in combination with other features.

LIST OF REFERENCE NUMBERS 10 irradiation facility
11 ion source
12 low energy beam transfer line
13 pre-accelerator
15 accelerator unit
17 beam guide
19 measurement room
20 particle beam
21 treatment room
22 deflection and modulation device
30 target point
34 target volume
36 arrow
40, 42 scanner magnets for lateral deflection of the particle beam 44 double-wedge system for longitudinal deflection (=braking) of the particle beam
46 motion sensing device
50 arrow to illustrate motion
52 clinical target volume
54 safety margin (IM)
56 area at risk or organ at risk (OAR)
58 distribution curve of a simple planned nominal dose distribution
60 distribution curve of a conventional dose distribution
62 distribution curve of a motion-corrected nominal dose distribution
64 distribution curve of a motion-corrected dose distribution
71 CAT or MRI system
72 PET camera
73 distance sensor
77 body
78 support surface
81 device for creating a data set
82 device for quantitative sensing of motions
86 controller
87 control line
101 to 108 steps of the planning method
111 to 114 steps of the irradiation method

The invention claimed is:

1. Method for irradiation planning for calculating a mean motion to be expected of target points of a target volume based on a motion model, taking into account mean motion to be expected of the target points of the target volume in irradiation planning in such a manner that a deviation of an expected dose deposition from a nominal dose for each target point is determined, and the nominal dose for each target point is corrected on the basis of the deviation, and a corrected nominal dose is generated irradiation of a moving target volume located in a body with a particle beam irradiation facility by means of rescanning, having the following steps:
    defining the target volume in a reference condition of the motion wherein the target volume has different motion conditions,
    dividing the target volume among a plurality of target points that can be individually approached with a particle beam,
    defining a number of rescanning passes in which said target points of the target volume are approached,
    calculating a nominal dose for each of said target points to be deposited in said target points of the target volume,
    calculating a mean motion to be expected of the target points of the target volume based on a motion model, taking into account the mean motion to be expected of the target points of the target volume in the irradiation planning in such a manner that the deviation of the expected dose deposition from the nominal dose for each target point is determined, and the nominal dose for each target point is corrected on the basis of the deviation, and a corrected nominal dose is generated,
    dividing the corrected nominal dose among the rescanning passes in different motion conditions,
    generating control parameters for the irradiation facility, wherein the control parameters comprise a particle count per target point and rescanning pass to be applied;
    wherein a patient model, a mathematical function, and/or a breathing study is taken into account for determining the motion model; and
    wherein the corrected nominal dose per target point is divided in different motion conditions among the rescanning passes.

2. Method for irradiation planning according to claim 1, wherein the motion model of the target volume has different motion conditions, and the nominal dose per target point is divided among the rescanning passes, weighted according to the motion condition.

3. Method for irradiation planning according to claim 1, wherein the motion model of the target volume is cyclic, and the reference condition occurs repeatedly, so that the nominal dose per target point is divided evenly among the rescanning passes through a time-based coupling of the rescanning passes to the motion model.

4. Method for irradiation planning according to claim 1, wherein the expected dose distributions for the target points of the target volume are calculated for the iso-energy layers of the particle beam.

5. Method for irradiation planning according to claim 1, wherein the iso-energy layers are each approached by the particle beam upon the occurrence of a defined motion condition.

6. Method for irradiation of a moving target volume located in a body with a particle beam irradiation facility by means of rescanning, wherein the target volume has different motion conditions, having the following steps:
    generating control parameters, wherein the mean motion to be expected of the target points of the target volume is taken into account in the irradiation planning by means of a motion model in such a manner that the deviation of the expected dose deposition from the nominal dose for each target point is determined, the nominal dose for each target point is corrected on the basis of the deviation, and a corrected nominal dose is generated,
    loading the irradiation plan with the control parameters, which was produced in advance of the irradiation, into a control unit,
    detecting the motion of the target volume during the course of the irradiation using a motion sensing device, and generation of additional control parameters by means of the motion sensing device,
    controlling the particle beam by means of the control parameters stored in the irradiation plan and by means of the additional control parameters in order to irradiate the target volume with the particle beam with the motion of the target volume being taken into account
    dividing the corrected nominal dose among rescanning passes in different motion conditions;
    wherein the patient model, a mathematical function, and/or a breathing study is taken into account for determining the motion model;
    wherein the motion model of the target volume has different motion conditions, and the corrected nominal dose per target point is divided among the rescanning passes.

7. Method for irradiation according to claim 6, wherein the particle count of the particle beam is varied by means of the control parameters stored in the irradiation plan and by means of the additional control parameters generated with the motion sensing device.

8. Method for irradiation according to claim 6, wherein the nominal dose per target point is divided among the rescanning passes, weighted according to the motion condition.

9. Method for irradiation according to claim 6,
wherein the motion of the target volume is cyclic, and the reference condition occurs repeatedly, so that the nominal dose per target point is divided evenly among the rescanning passes through a time-based coupling of the rescanning passes to the motion.

10. Method for irradiation according to claim 6,
wherein the expected dose distributions for the target points of the target volume are calculated for iso-energy layers of the particle beam.

11. Method for irradiation according to claim 6,
wherein the iso-energy layers are each approached by the particle beam upon the occurrence of a defined motion condition.

12. Irradiation facility, comprising:
an accelerator unit,
a device for creating a data set that provides control parameters, for a control unit, by which means a corrected dose distribution is divided among a number of rescanning passes in a target volume while taking into account a motion model,
wherein a mean motion to be expected of the target points of the target volume is taken into account for determining the motion model,
a motion sensing device for sensing the motion of the target volume before or during the irradiation with the particle beam so that corrected additional control parameters can be generated by means of the motion sensing device and can be made available for controlling the radiation facility,
the control unit for controlling the accelerator unit with the use of the control parameters and the additional control parameters in order to administer a corrected dose distribution in the target volume with the particle beam with the motion of the target volume being taken into account,
wherein the control unit of the irradiation facility is configured to distribute the corrected nominal dose among the rescanning passes in different motion conditions;
wherein a patient model, a mathematical function, and/or a breathing study is taken into account for determining the motion model; and
wherein the control unit of the irradiation facility is configured for dividing the corrected nominal dose in different motion conditions among the rescanning passes.

13. Irradiation facility according to claim 12,
wherein the particle count of the particle beam is varied by means of the control parameters stored in the irradiation plan and by means of the additional control parameters generated by means of the motion sensing device.

14. Irradiation facility according to claim 12,
wherein the control unit of the irradiation facility is configured to divide the nominal dose per target point among the rescanning passes, weighted according to the motion condition.

15. Irradiation facility according to claim 12,
wherein the motion sensing device detects a cyclic motion of the target volume on the basis of the reference condition, and
wherein the control unit of the irradiation facility is configured to distribute the corrected nominal dose per target point evenly among the rescanning passes through a time-based coupling of the rescanning passes to the motion.

16. Irradiation facility according to claim 12,
wherein the control unit of the irradiation facility is configured to approach the target points of the target volume in iso-energy layers of the particle beam with a particle count corresponding to the corrected dose distribution.

17. Irradiation facility according to claim 12,
wherein the control unit of the irradiation facility is configured to approach each of the iso-energy layers with the particle beam upon the occurrence of a defined motion condition on the basis of the additional control parameters of the motion sensing device.

18. Irradiation facility according to claim 12,
wherein an average expected motion of the target points of the target volume for determining the motion model is obtained by at least one of the patient model, the motion function or the breathing study.

19. Method for irradiation planning according to claim 1, wherein the function includes $$F(i, N_j, P_m) = \sum_i \left( D_{plan} - \sum_m P_m \cdot D_{i,m}\left(\sum_j N_j\right) \right)^2$$

where $$D_{i,m}\left(\sum_j N_j\right)$$

represents the dose deposited in the target point i, in the motion condition m, and Pm represents the probability of striking the target volume in the motion condition m.

20. Method for irradiation planning according to claim 1, wherein a dose deposited at a target point is calculated from a weighted average of dose contributions from all expected motion conditions.

* * * * *